United States Patent [19]

Crump et al.

[11] Patent Number: 4,466,836

[45] Date of Patent: Aug. 21, 1984

[54] SET RETARDING COMPOUNDS FOR USE IN CEMENT SLURRIES

[75] Inventors: Druce K. Crump, Lake Jackson; David A. Wilson, Richwood, both of Tex.

[73] Assignee: The Dow Chemical Company, Midland, Mich.

[21] Appl. No.: 489,441

[22] Filed: Apr. 28, 1983

[51] Int. Cl.$^3$ .............................................. C04B 7/35
[52] U.S. Cl. ...................................... 106/90; 106/315
[58] Field of Search ................................ 106/90, 315

[56] References Cited

U.S. PATENT DOCUMENTS

| | | | |
|---|---|---|---|
| 3,346,487 | 10/1967 | Irani et al. | 106/90 |
| 3,346,488 | 10/1967 | Lyons et al. | 106/90 |
| 3,409,080 | 11/1968 | Harrison | 166/31 |
| 3,654,151 | 4/1972 | King et al. | 106/90 |
| 3,657,134 | 4/1972 | King et al. | 106/90 |
| 3,794,506 | 2/1974 | Schmidt et al. | 106/90 |
| 3,865,803 | 2/1975 | Falkehag | 260/124 A |
| 3,964,921 | 6/1976 | Persinski et al. | 106/90 |
| 4,040,854 | 8/1977 | Persinski et al. | 106/90 |
| 4,066,469 | 1/1978 | Shiel et al. | 106/89 |
| 4,225,361 | 9/1980 | Joseph | 106/111 |
| 4,401,473 | 8/1983 | Kleiner et al. | 106/109 |

OTHER PUBLICATIONS

Chem. Abstracts: 97, 112352a—"Plugging Composition for Cementing Oil and Gas Wells", Dytyuk, L. T. et al.
Chem Abstracts: 97, 26178a—"Plugging Fluids for Cementing Deep Petroleum and Gas Wells", Alekseev, P. D., et al.
Chem. Abstracts: 98, 58912p—"Improvement of Casing Cementation in Deep and Ultradeep Wells, Part 2, Deep Well Cements and Additives," Arens, K. H. et al.
SU-640-019, "Plugging Mixture for High-Temperature Oil or Gas Wells—Comprises Portland Cement and 1-Hydroxy Ethylidene-Phosphonic Acid Sodium or Potassium Salt", Khariv I YU.
"Additives Tailor Cement to Individual Wells", P. N. Parker, C. Clement, *The Oil and Gas Journal*, Mar. 14, 1977, vol. 75.

*Primary Examiner*—James Poer
*Attorney, Agent, or Firm*—A. C. Ancona

[57] ABSTRACT

The process of employing as a cement setting retarder a compound which is a phosphonomethylated derivative of a dimer or polymer which is the reaction product of ethylene dichloride or epichlorohydrin with aminoethylpiperazine wherein at least 50% of the amine hydrogen substituents are phosphonomethyl groups or an alkali metal, alkaline earth metal or ammonium salt thereof.

3 Claims, No Drawings

SET RETARDING COMPOUNDS FOR USE IN CEMENT SLURRIES

BACKGROUND OF THE INVENTION

The invention pertains to aqueous hydraulic cement slurry compositions containing particular set retarders which are phosphonic acid derivatives of adducts of aminoethylpiperazine and ethylene dichloride.

Hydrophobic-substituted phosphonic or phosphinic acids and their alkali metal salts have been used in cements, primarily soil/cement mixtures, to improve the freeze-thaw properties and salt-resistance. Six- to eighteen-carbon alkyl phosphonic acids or their alkali metal salts are so described in U.S. Pat. No. 3,794,506. A plugging mixture for high temperature oil and gas wells comprising Portland cement and 1-hydroxy ethylidenephosphonic acid trisodium or tripotassium salts as set time extenders is described in Derwent abstract 71376B/39 (1979) of USSR Pat. No. 640,019. The use of these phosphonate salts at temperatures of 75° to 150° C. in amounts of 0.1–0.3% by weight is described in the abstract.

Other organic phosphorous acid derivatives are taught to be useful additives in cement compositions as turbulence-inducing and flow-property improver additives (U.S. Pat. Nos. 3,964,921 and 4,040,854, respectively). Another turbulence-inducer is a pyrolysis product of urea and a bis(alkylenepyrophosphate) (U.S. Pat. No. 3,409,080).

Alkylene diphosphonic acids and their water soluble salts are described as set time extenders and water reducing agents for gypsum plasters (U.S. Pat. No. 4,225,361). Lignins which have been phosphonoalkylated through an ether linkage or corresponding sulfonates, sulfides, hydroxyl or amine derivatives are taught to be useful primarily as dispersants or surfactants (U.S. Pat. No. 3,865,803) and are also said to be useful as "cement additives" without indicating specific uses.

Ultra-rapid hardening Portland cement compositions are described which contain various acid salt additives (U.S. Pat. No. 4,066,469). It states that use of acid phosphates as the acid salt additives is excluded since the phosphates have a characteristically powerful retarding property peculiar to them.

Most of the cement used in oil wells is called portland cement. Portland cement is manufactured by calcining raw materials consisting of limestone, clay, shale, and slag together at 2,600° to 2,800° F. in a rotary kiln.

The resulting material, is cooled and interground with small percentages of gypsum to form portland cement. In addition to the above raw materials, other components such as sand, bauxite, iron oxide, etc., may be added to adjust the chemical composition depending upon the type of portland cement desired.

The principal components of the finished portland cement are lime, silica, alumina, and iron. These components form the following complex compounds: Tricalcium aluminate, ($3CaO.Al_2O_3$), tetracalcium aluminoferrite, ($4CaO.Al_2O_3.Fe_2O_3$), tricalcium silicate, ($3CaO.SiO_2$), and dicalcium silicate, ($2CaO.SiO_2$).

When water is added to cement, setting and hardening reactions begin immediately. The chemical compounds in the cement undergo the processes of hydration and recrystallization which results in a set product. The maximum amount of water that can be used with an oil-well cement is the amount which can be added before solids separation occurs. The minimum amount of water is the amount required to make the slurry pumpable. Therefore, the normal water ratio is governed by the maximum and minimum limits for a particular class of cement.

Thickening time is the time that the cement remains pumpable in the well. This is the most critical property of an oil-well cement. The thickening time has to be long enough to be pumped into place and short enough to permit operations to resume quickly. Generally, 3 hours provides the necessary placement time plus a safety factor.

Other factors, such as fluid loss, viscosity and density must be taken into consideration and additives are known to the art-skilled which affect each of these factors as well as that of set, or thickening, time as mentioned above. Another parameter which has an effect on set time is temperature. Cement sets more rapidly as the temperature increases. This must be taken into consideration particularly when pumping cement into deeper wells since temperature increases as the depth of the well becomes greater. Temperature also affects the strength of the cement, the strength becoming less as the temperature increases.

Because of this temperature effect, it is important to retard the setting of the cement employed in the deeper wells.

It has now been discovered that certain new phosphonomethylated compounds are useful in aqueous cement slurries as set retarding additives. Some of these compounds are chelating agents, while others are useful as threshold agents in retarding the precipitation of metal ions from aqueous solution. However, not all such compounds are useful as cement set-retarders.

Polymethylenephosphonic acid derivatives of polymers of aminoethylpiperazine have been found to be superior scale inhibitors. The polymers are formed by reacting aminoethylpiperazine with a dihalo, diepoxy or epoxyhalo compound and then reacting the resulting polymer with phosphorous acid and formaldehyde to form the polymethylenephosphonic acid polyamine of the invention. These compounds have been disclosed in our copending U.S. patent application Ser. No. 425,025, filed Sept. 27, 1982 and have now been found useful as cement set-retarding additives.

SUMMARY OF THE INVENTION

The compounds useful as cement retarders in aqueous cement slurries are methylene phosphonic acid derivatives having the following formula:

$$A(BA)_m$$

wherein A is an organic radical having the formula

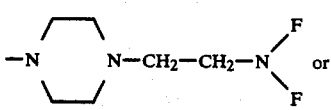

or

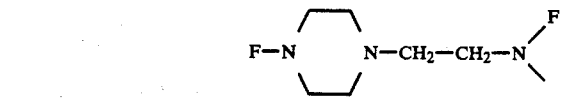

wherein F is hydrogen, hydroxyethyl, hydroxypropyl,

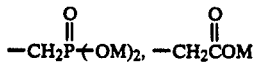

or BA wherein M is hydrogen, an alkali metal or ammonium, and wherein B is a divalent radical derived from a dihalo, or haloepoxy organic compound having one of the following structures

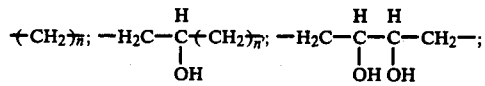

wherein n is 1–10, n' is 1–3, m is 1–10 and at least 50% of the F groups are

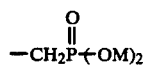

groups.

DETAILED DESCRIPTION OF THE INVENTION

The compounds useful for retarding the setting of cement are made by reacting aminoethylpiperazine (AEP) with a dihalo or epoxyhalo compound and subsequently reacting the polymer formed thereby with phosphorous acid and formaldehyde at a low pH, usually provided by the presence of a mineral acid, e.g. hydrochloric.

The AEP can be reacted with any number of dihalo or epoxyhalo compounds in order to form a dimer or polymer. Any suitable epihalohydrin may be reacted, epichlorohydrin being preferred.

Saturated dihalides having the formula $X(CH_2)_nX$, where X may be chlorine, bromine, iodine or combinations thereof and wherein n is an integer of from 1 to about 10, but preferably 2 to 6, may be employed. Thus, for example, methylene chloride, ethylene dichloride, 1,2- or 1,3-dichloropropane, 1,4- or 1,2-dibromobutane and the like may be employed.

In making the polymer the reactants are employed in an amount of from about 0.2 to about 1 mole of the chain extender compound, preferably about 0.25 to about 0.6, i.e. dihalo- or epoxyhalo- compound, per mole of AEP.

The phosphonomethylation (Mannich reaction) is then carried out on the dimeric or polymeric product in the presence of a strong acid to maintain the pH at less than 1.

While the reaction will proceed at temperatures over a wide range, i.e., from 85° to 150° C., it is preferred that the temperatures of the reaction medium be maintained at the refluxing temperatures. The reaction is preferably conducted at atmospheric pressure.

Approximately equimolar amounts of formaldehyde and phosphorous acid are employed for the phosphonomethylation of the amine. The preferred process will use an amount of aldehyde equivalent to the amine hydrogens available and a slight stoichiometric excess of the phosphorous acid.

The compounds of the present invention which are useful as set retarders for cement as well as additional reactants and reaction parameters are disclosed in our copending U.S. application Ser. No. 425,025, filed Sept. 27, 1982.

Table I shows the use of some of the above identified products in retarding the setting of cement. The test procedure for the determination of retardation of setting is as follows:

1. The following ingredients were weighed:
   cement—100 g
   water—38 g
   additive—0.2 g active
2. Water and liquid additive were mixed;
3. Cement was added to liquid, the bottle tightly closed and shaken to mix;
4. Bottle was placed in a pre-heated 180° F. bath;
5. Setting of cement was checked after 6 and 24 hours. A blank (no additive) was run for comparison with each of the additives.

TABLE I

| Additive* | Checked at: | |
| --- | --- | --- |
| mol ratio EDC/AEP | 6 hours | 24 hours |
| 0.26 | Retarded, not set | Retarded, not set |
| 0.46 | " | " |
| 0.50** | " | " |
| 0.56 | " | " |
| 0.81 | " | " |
| Blank | Set | Set |

*The additive is the phosphonomethylated product identified by the mol ratio of EDC/AEP.
**EPI was used in place of EDC for making this additive.

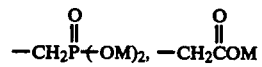

or BA wherein M is hydrogen, an alkali metal, alkaline earth metal or ammonium radical, and wherein B is a divalent radical derived from a dihalo or haloepoxy organic compound having one of the following structures
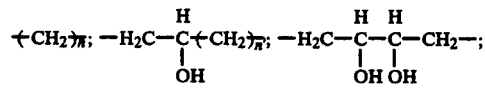
wherein n is 1-10, n' is 1-3, m is 1-10 and at least 50% of the F groups are
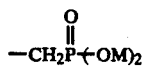
groups.
3. The process of claim 2 wherein m is 1 or 2, B is
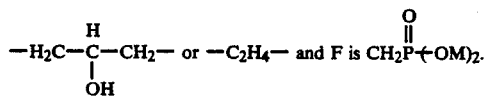

We claim:

1. In a process for retarding the setting of an aqueous cement slurry which comprises adding to said slurry an organic phosphonate, the improvement which comprises employing a compound which is the phosphonomethylated reaction product of a dihalo or haloepoxy organic compound with aminoethylpiperazine wherein the mole ratio of dihalo or haloepoxy compound to the amine compound is from about 0.20 to about 1.0, and wherein at least 50% of the amine hydrogens are phosphonomethylated.

2. In a process for retarding the setting of an aqueous cement slurry which comprises adding to said slurry an organic phosphonate, the improvement which comprises employing a compound of the formula

wherein A is an organic radical having the formula

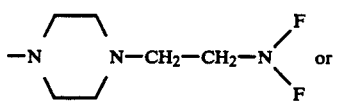

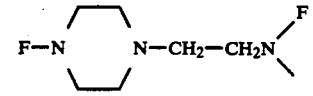

wherein F is hydrogen, hydroxyethyl, hydroxypropyl,